US012667462B2

(12) United States Patent
Aksu et al.

(10) Patent No.: US 12,667,462 B2
(45) Date of Patent: Jun. 30, 2026

(54) IMPLANTABLE MANDIBULAR JOINT PROSTHESIS AND CORRESPONDING PRODUCTION METHOD

(71) Applicant: Karl Leibinger Asset Management GmbH & Co. KG, Mühlheim an der Donau (DE)

(72) Inventors: Adem Aksu, VS-Schwenningen (DE); Ralf Leibinger, Mühlheim/Donau (DE); Frank Reinauer, Emmingen-Liptingen (DE); Tobias Wolfram, Dreieich (DE)

(73) Assignee: Karl Leibinger Asset Management GmbH & Co. KG, Mühlheim an der Donau (DE)

( * ) Notice: Subject to any disclaimer, the term of this patent is extended or adjusted under 35 U.S.C. 154(b) by 597 days.

(21) Appl. No.: 18/044,342

(22) PCT Filed: Sep. 15, 2021

(86) PCT No.: PCT/EP2021/075368
§ 371 (c)(1),
(2) Date: Mar. 7, 2023

(87) PCT Pub. No.: WO2022/058374
PCT Pub. Date: Mar. 24, 2022

(65) Prior Publication Data
US 2023/0329872 A1 Oct. 19, 2023

(30) Foreign Application Priority Data
Sep. 16, 2020 (DE) ..................... 10 2020 211 582.6

(51) Int. Cl.
*A61F 2/30* (2006.01)
*A61L 27/16* (2006.01)

(52) U.S. Cl.
CPC ............ *A61F 2/3099* (2013.01); *A61L 27/16* (2013.01); *A61F 2002/30004* (2013.01); *A61F 2002/30991* (2013.01); *A61F 2002/30993* (2013.01)

(58) Field of Classification Search
CPC .......... A61F 2/3099; A61F 2002/30004; A61F 2002/30991; A61F 2002/30993;
(Continued)

(56) References Cited

U.S. PATENT DOCUMENTS

| | | | |
|---|---|---|---|
| 6,132,466 | A | 10/2000 | Hoffman et al. |
| 7,879,275 | B2 | 2/2011 | Smith et al. |
| 2020/0008945 | A1 | 1/2020 | Ferri |

FOREIGN PATENT DOCUMENTS

| | | |
|---|---|---|
| CN | 205626192 U | 10/2016 |
| DE | 694 29 210 T2 | 7/2002 |

(Continued)

OTHER PUBLICATIONS

International Search Report corresponding to PCT Application No. PCT/EP2021/075368, mailed Dec. 10, 2021 (German and English language document) (7 pages).

*Primary Examiner* — Yashita Sharma
(74) *Attorney, Agent, or Firm* — Dority & Manning, P.A.

(57) ABSTRACT

An implantable mandibular joint prosthesis includes a first implant part that has an artificial condyle that can be attached to a lower jawbone, a second implant part that has a joint surface that can be attached to a cranium and that forms an abutment for the artificial condyle The second implant part comprises includes a first component which is formed from a metal material and can be attached to the cranium, and a second component which is formed from a plastics material and forms the joint surface. The first component has a first connection surface and the second (Continued)

component has a second connection surface, wherein the first and second connection surfaces are mutually engagingly joined together.

16 Claims, 4 Drawing Sheets

(58) Field of Classification Search
CPC .. A61F 2002/30578; A61F 2002/30957; A61F 2002/30968; A61F 2002/30975; A61L 27/16; B29C 43/00; B29C 43/006; B29C 43/18; B29C 43/52; B29C 2043/181
See application file for complete search history.

(56) References Cited

FOREIGN PATENT DOCUMENTS

| | | | |
|----|-------------------|----|----------|
| EP | 0 203 719 | A1 | 12/1986 |
| EP | 3 003 225 | B1 | 1/2017 |
| JP | S61253055 | A | 11/1986 |
| JP | 2020507442 | A | 3/2020 |
| KR | 20190061449 | A | 6/2019 |
| KR | 10-2009324 | B1 | 10/2019 |
| WO | 2020/141774 | A2 | 7/2020 |

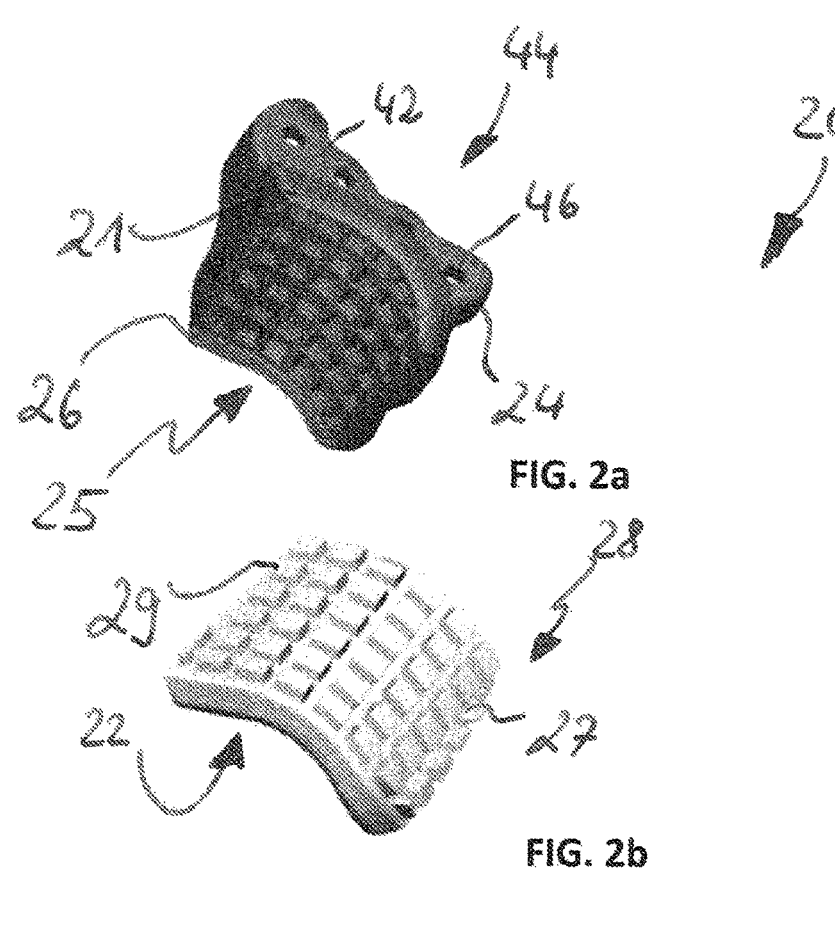
FIG. 2a
FIG. 2b
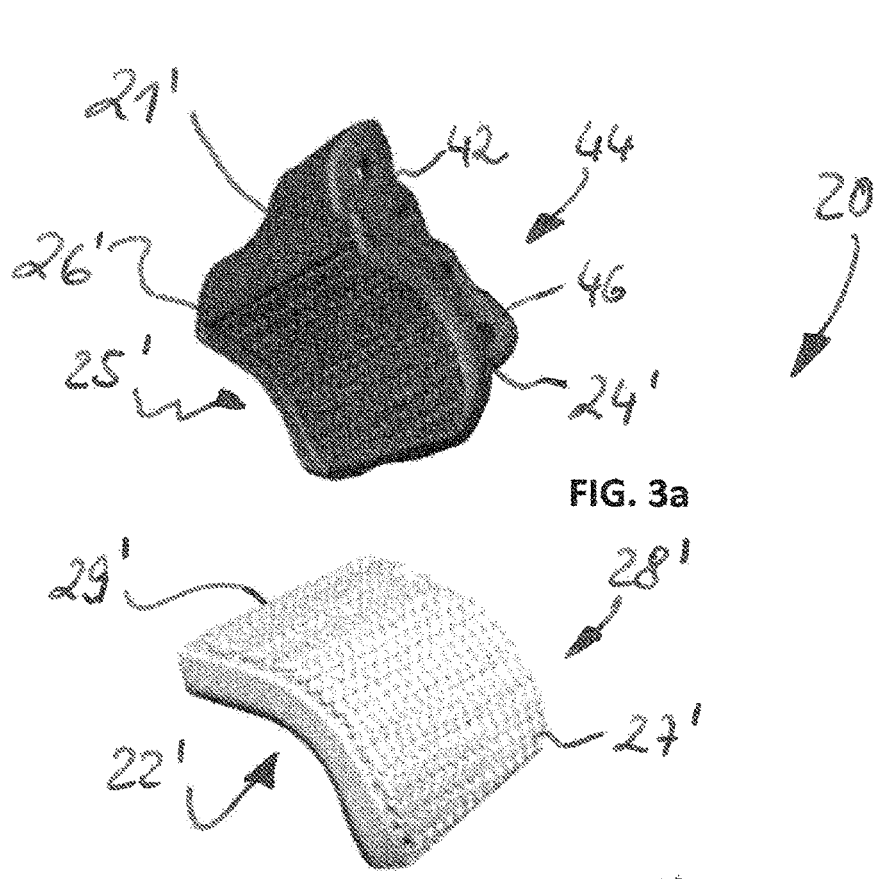
FIG. 3a
FIG. 3b

IMPLANTABLE MANDIBULAR JOINT PROSTHESIS AND CORRESPONDING PRODUCTION METHOD

BACKGROUND

The present invention relates to an implantable temporomandibular joint prosthesis comprising a first implant part having an artificial condyle that is attachable to a lower jaw and a second implant part having an articular surface that is attachable to a cranium, wherein the articular surface forms an abutment for the artificial condyle. The invention further relates to a corresponding method for producing an implantable temporomandibular joint prosthesis.

The temporomandibular joint (also referred to hereinafter as TMJ) is one of the most used and most important joints in the human body. It plays an essential role in guiding the movement of the mandible (lower jaw) during chewing, speaking, swallowing and stress management. It is constantly in motion even during sleep owing to swallowing movement. In order for the temporomandibular joint to be able to perform its sequences of movement, it is necessary for the shape of the articular surfaces, the condition of the teeth, the position of the teeth, the shape of the teeth and the muscles of mastication to form a functional system, which is subject to a certain degree of susceptibility to dysfunction owing to the multiplicity of components. The left and right temporomandibular joints always work together and form in this respect a functional unit.

However, if dysfunctions occur in the region of the temporomandibular joint, such as functional restrictions or diseases, the everyday quality of life of patients can become considerably impaired. In this case, restoration of correct joint structures is usually only possible by means of a surgical solution, i.e., by resection of the defective joint and replacement thereof with a temporomandibular joint prosthesis.

A temporomandibular joint prosthesis is, for example, known from EP 3 003 225 B1, which provides a mechanism allowing combined translational and rotational movement between skull and lower jaw, said movement involving sliding movement between surfaces. However, wear and tear can occur.

SUMMARY OF THE DISCLOSURE

It is an object of the present invention to provide an improved implantable temporomandibular joint prosthesis, by means of which the sliding movement of the surfaces is carried out as reliably and safely as possible and, at the same time, with little wear and tear.

The object is achieved by an implantable temporomandibular joint prosthesis having the features described herein. The solution according to the invention thus in particular consists in the fact that, in the case of a temporomandibular joint prosthesis of the type mentioned at the start, the second implant part has a first component which is formed from a metallic material and which is attachable to the cranium and a second component which is formed from a plastic and which forms the articular surface, and that the first component has a first connection surface and the second component has a second connection surface, wherein the first connection surface and the second connection surface are mutually engagingly and integrally connected to one another.

The implantable temporomandibular joint prosthesis according to the invention thus provides a reliable tribological pairing at the articular surface which forms the abutment for the condyle, by providing multiple components on the second implant part that mutually engage and are integrally connected via their connection surfaces, with the result that the connection of metal components and plastics components gives rise to a stable, low-wear articular surface for the tribological pairing. In particular, no "snap-in" or form-fitting mechanism is provided; instead, the abutment is in the form of an open-shell sliding surface based on the real surface of the human temporomandibular joint. The native muscle chain holds the two implant parts in position and allows the restoration of realistic joint function.

The condyle and the temporal bone can be left in their 3D contour, and the implantable temporomandibular joint prosthesis according to the invention is therefore patient-specifically scalable and pathologically usable.

In a preferred development of the temporomandibular joint prosthesis, in order to achieve a form fit between the two connection surfaces of the first component that is durable and is stressable with respect to transverse sliding, the first connection surface can be provided with recesses into which projections arranged on the second connection surface engage.

In a further preferred development, the recesses in the first connection surface of the first component and the corresponding projections of the second component can be homogeneous or inhomogeneous to ensure the form fit of the connection surfaces. Here, the recesses can be homogeneous or inhomogeneous with respect to both their shape and their distribution on the connection surface. For example, a homogeneous variant can consist in the uniform arrangement of cross-sectionally square recesses in both directions of extent of the connection surface, whereas an inhomogeneous variant can be designed with a plurality of recess types which extend on the connection surface in different directions with differing numbers, for instance, or break the uniformity in some other way. This also applies conversely to the abovementioned projections as elements of the second connection surface that are complementary to the recesses.

In a further preferred development of the temporomandibular joint prosthesis according to the invention, the size of the recesses on the first connection surface of the first component can, for example, be between 1 μm and 2000 μm, and so a broad size range is covered with respect to the individual extent of the particular recesses. However, other sizes of individual extents are also conceivable.

In a further preferred development of the temporomandibular joint prosthesis according to the invention, in which the tribological pairing of the joint has a minimum space requirement, the first and the second connection surface can be in the form of mutually congruent surfaces which substantially overlap one another. As a result, the articular surface in question can be provided in exactly the required extent.

In another preferred development, in order to ensure a natural sequence of movement with the temporomandibular joint prosthesis according to the invention, the first connection surface can be concave. However, a plurality of different curvatures with different radii of curvature and different directions, in particular directions orthogonal to one another, are also conceivable.

In a further preferred development, the two components of the second implant part can be particularly stably connected in that the first component and the second component form a fused composite via their mutually engaging connection surfaces. Besides the form fit achieved by the shape of the connection surfaces, stability is then based in particular on the integral bond, which can, for example, be realized by applying heat to the connection surfaces, possibly additionally under pressure and/or vacuum.

An articular surface having very good sliding properties is achieved in a further preferred development in that the first component is made of titanium or a titanium alloy and in that the plastic of the second component is made of a thermoplastic, in particular PE-UHMW as a thermoplastic. However, other combinations of metallic and plastic-like materials are also conceivable.

In another preferred development, in which the articular surface together with the condyle forms a particularly easy-to-handle tribological pairing, the first implant part can be made of a ceramic, a PEEK material, a metallic material or a combination of these materials.

In a further preferred development, in order to be able to prevent lateral slipping in a normal sequence of movement, the first component can have an edge region which at least regionally grips around the second component. The edge region offers further stabilization of the connection surfaces to one another. In this connection, the edge region can be arranged at the side ends of the articular surface, whereas the front and rear end faces thereof can be free of the edge region. However, other configurations of the edge region are also conceivable.

In a further preferred development, in order to be able to align the two implant parts of the temporomandibular joint prosthesis according to the invention appropriately relative to one another and, at the same time, mount them stably on the mutually opposing body regions, the first and the second implant part can be detachably attachable to the lower jaw and the cranium, respectively, by means of a first and a second attachment part, respectively, thereby also making later removal or exchange possible in a simple manner.

In a further preferred development, the first and the second attachment part can each have a hole arrangement, through the holes of which immobilization means assigned thereto can engage in a structure of the lower jaw and the cranium, respectively. The respective hole arrangement can be matched to the respective local circumstances with respect to both positioning and number of holes. For example, the first attachment part of the first implant part can be provided with six holes which are evenly spaced on the attachment part, whereas the hole arrangement of the second attachment part of the second implant part is provided with only four holes. However, other hole arrangements are also each conceivable. Screws as immobilization means, for instance, can reach through the holes of the hole arrangement. The immobilization means are not limited to screws.

The above object is also achieved by a method for producing an implantable temporomandibular joint prosthesis, comprising at least the following steps: providing a first implant part having an artificial condyle that is attachable to a lower jaw; providing a second implant part having an articular surface that is attachable to a cranium; wherein the articular surface forms an abutment for the artificial condyle; wherein the second implant part has a first component which is formed from a metallic material and which is attachable to the cranium and a second component which is formed from a plastic and which forms the articular surface; mutually and integrally connecting a first connection surface of the first component to a second connection surface of the second component.

The mutually engaging and integral connection of metal component and plastics components forms a stable articular surface for the tribological pairing.

In a preferred development of the production method according to the invention, which offers increased stability and durability of the articular surface, heat and pressure and/or vacuum are applied to the first and the second component during connection of the first and the second connection surface.

In a further preferred development, the first component and the second component, during connection, are fused together to form a fused composite, and so the components are joined together in an integral bond.

In a further preferred development of the production method according to the invention, the fused composite is formed at the first and the second connection surface by inserting the first component into a fusion mold and at least partially filling a volume encompassed by the first component in the region of the articular surface with the plastic of the second component in powder form before the application of heat, pressure and/or vacuum.

In a further preferred development of the production method according to the invention, the fusion mold is multipieced and completely encloses the first component and the second component during connection thereof to one another to form a fused composite, and so the components are appropriately integrally connected and can then be demolded from the fusion mold without any difficulties.

The above configurations and developments can be combined with one another as desired where appropriate. Further possible configurations, developments and implementations of the invention also encompass combinations of features of the invention that have not been explicitly mentioned, which features have been described above or will be described below with regard to the exemplary embodiments.

DESCRIPTION OF THE DRAWINGS

The invention will be more particularly elucidated below on the basis of exemplary embodiments in the figures of the drawing. Shown here in a partially schematized illustration are:

FIG. 2a, 2b perspective side views of the first component and second component of the second implant part of the first embodiment;

FIG. 3a, 3b perspective side views of the first component and second component of the second implant part of a second embodiment;

In all the figures, identical or functionally identical elements and devices have been provided with the same reference signs, unless otherwise stated.

DETAILED DESCRIPTION

Figure 1:
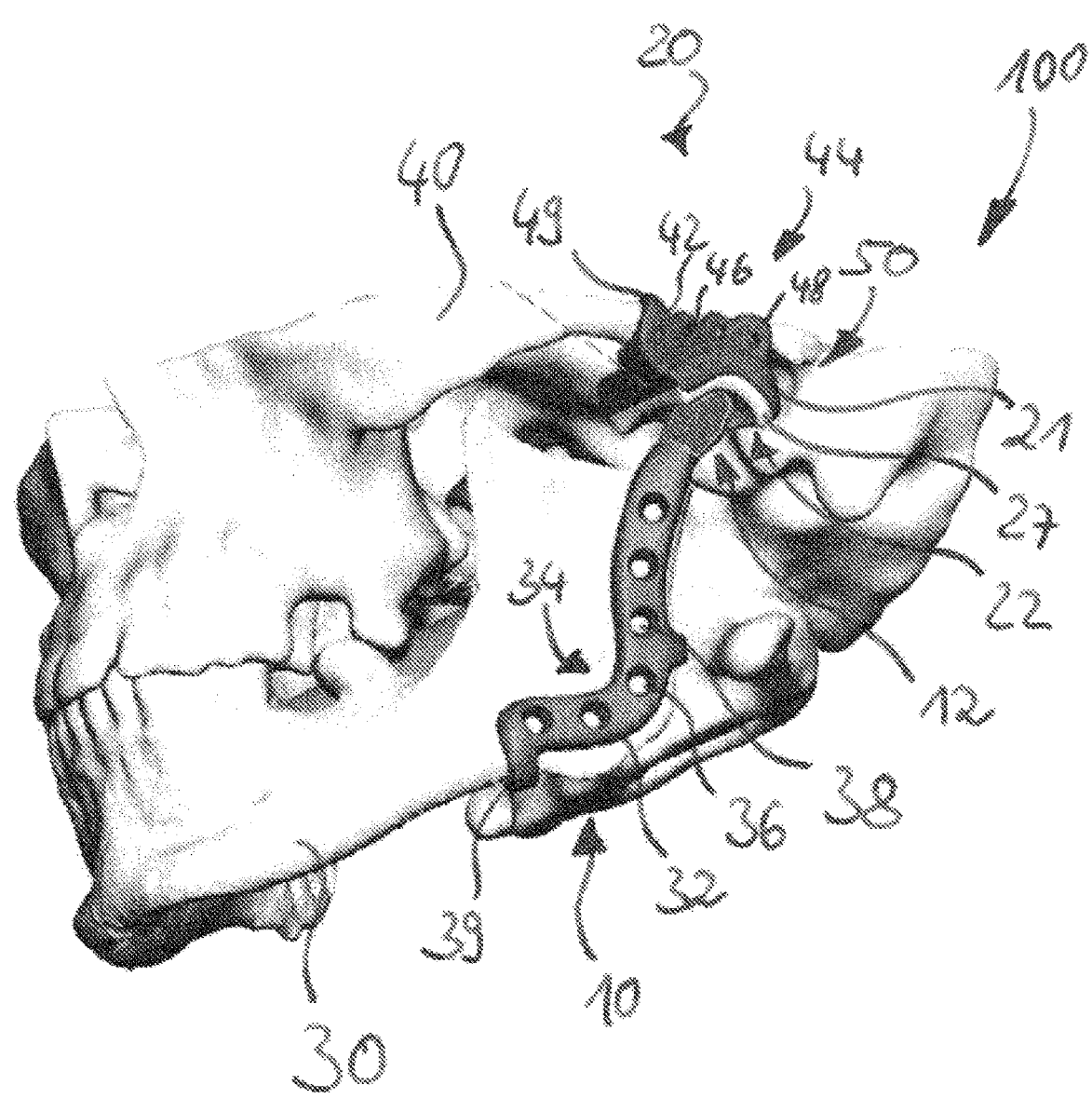
FIG. 1 a perspective side view of a first embodiment of the temporomandibular joint prosthesis, which embodiment is according to the invention, comprising a first and a second implant part in the implanted state.

FIG. 1 shows a perspective side view of a first embodiment of the temporomandibular joint prosthesis according to the invention, comprising a first and a second implant part in the implanted state.

FIG. 1 shows an implantable temporomandibular joint prosthesis, indicated as a whole by 100, comprising a first implant part 10 and a second implant part 20, which together form a tribological pairing. The first implant part 10 is attached to the depicted lower jaw 30 (mandible) and is provided with a condyle 12 at its end facing the second implant part 20. The second implant part 20 is attached to the cheekbone (os zygomaticum) of the cranium 40 and is provided with an articular surface 22 which faces the condyle 12 and which forms an abutment for the condyle 12 of the first implant part 10.

The second implant part 20 has a first component 24 which is formed from a metallic material and which is attached to the cranium 40, whereas the articular surface 22 is formed from a second component 27 which is formed from a plastic. The first component 24 has a first connection surface 25 and the second component 27 has a second connection surface 28 (cf. FIGS. 2 and 3), which connection surfaces cannot be seen in FIG. 1 because the connection surfaces 25, 28 face each other and the first connection surface 25 and the second connection surface 28 are mutually engagingly and integrally connected to one another, and so only the articular surface which is formed on the side facing away from the connection surfaces 25, 28 and which faces the viewer can be seen in FIG. 1.

At the second implant part 20, the first component 24 is made of titanium and the plastic of the second component 27 is made of a thermoplastic, for example PE-UHMW (ultra-high-molecular-weight polyethylene), whereas the first implant part 10 is for example made of titanium. The first component 24 and the second component 27 of the second implant part 20 form a fused composite 50 via their mutually engaging connection surfaces 25, 28.

At the first component 24 of the second implant part 20, there is formed at the articular surface 22 an edge region 21 which regionally grips around the articular surface 22 on the side of the second implant part 20 facing the viewer and on the side of the second implant part 20 facing away from the viewer.

FIG. 1 further shows that the two implant parts 10, 20 are respectively detachably attached to the lower jaw 30 and the cranium 40 by means of a respective attachment part 32, 42, i.e., by means of a first and a second attachment part 32, 42, respectively. The first attachment part 32 has a first hole arrangement 34 and the second attachment part 42 has a second hole arrangement 44, through the holes 36, 46 of which screws as immobilization means 38, 48 grip the respective structure of the lower jaw 30 and the cranium 40.

The first implant part 10 is designed in the manner of a flat frame, the curvature of which follows that of the ascending branch of the mandible 30 and is immobilized thereon with six screws 38. Said screws 38 reach through evenly spaced holes 36 of the first hole arrangement 34. At the end facing away from the condyle 12 and approximately in the middle thereof, there is arranged on the first attachment part 32 a web 39 in each case, which web 32 projects transversely from the attachment part and grips around the bone of the mandible 30.

The second implant part 20 has, in the region thereof facing away from the articular surface 22, the second attachment part 42, which extends centrally from the first connection surface 25 of the first component in the direction facing away from the second connection surface 28 and has a second arrangement 44 of evenly spaced holes 46. Screws 48 as immobilization means hold the second implant part 20 on the cheekbone of the cranium 40. In addition, a web 49 which grips around the cheekbone of the cranium 40 is arranged at the frontal end of the second attachment part 42.

FIGS. 2a and 2b show perspective side views of the first component and second component of the second implant part 20 of the first embodiment, as already partially explained in connection with FIG. 1.

According to FIG. 2a, the recesses 26 of the first connection surface 25 are evenly distributed, and according to FIG. 2b, these are accommodated in the connected state by the cuboid projections 29 of the second connection surface 28.

FIGS. 3a and 3b show perspective side views of the first component and second component of the second implant part 20' of a second embodiment.

The second embodiment merely differs with respect to the design of the recesses 26' on the first component 24' and the associated projections 29' on the second component 27'. FIG. 3a shows the first component 24' having the first connection surface 25' and the edge region 21', which first component 24' faces the viewer, and so it is possible to clearly see the recesses 26' into which projections 29' according to FIG. 3b arranged on the second connection surface 28' engage when connection has been made to said second connection surface 28'.

The projections 29' of the second connection surface 28' according to FIG. 3b are in the form of raised polylines, which differ from one another in shape and are inhomogeneous in this respect.

The connection surfaces 25, 25', 28, 28' of the first component 24, 24' and the second component 27, 27' are in the form of mutually congruent surfaces which overlap one another. In addition, the connection surfaces 25, 25' of the first component 24, 24' each form a concave shape in cross section and each have a curvature with a changing radius of curvature. In addition, the second implant part 20, 20' has, at the articular surface 22, 22', an edge region 21, 21' which regionally grips around the articular surface 22, 22'.

Figure 4:
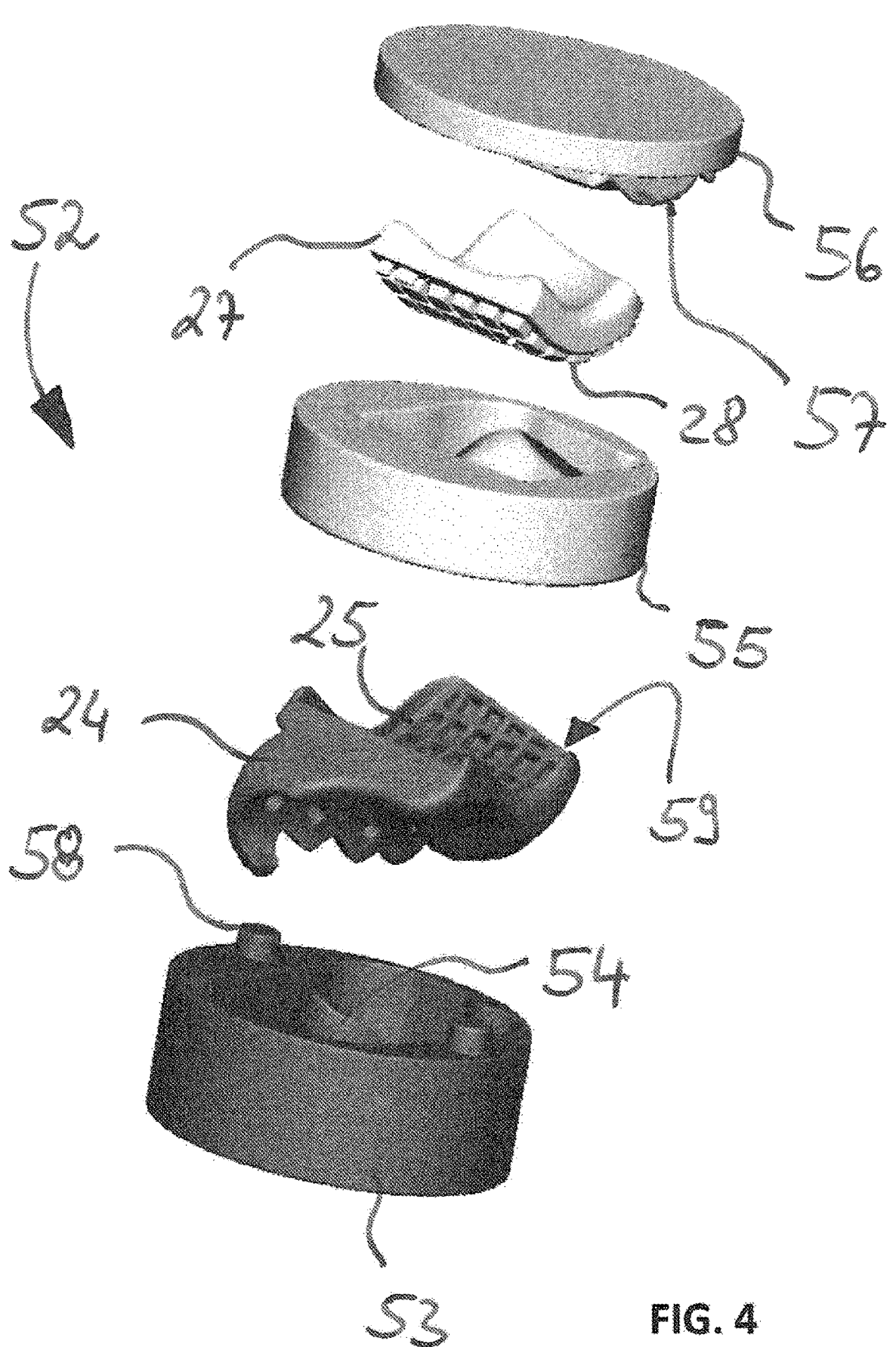
FIG. 4 an exploded perspective side view of a third embodiment, wherein the first component of the second implant part is inserted into a fusion mold for connection to the second component.

FIG. 4 is an exploded perspective side view of a third embodiment, wherein the first component of the second implant part is inserted into a fusion mold for connection to the second component, and FIGS. 5a-5d are perspective side views of the third embodiment that show the connection of the first component to the second component of the second implant part in the fusion mold in the chronological sequence thereof.

FIGS. 4 and 5 schematically depict one embodiment of the production method for the second implant part 20, 20' of the temporomandibular joint prosthesis 100, which embodiment will be explained with reference to the second implant part 20. According to FIG. 4, the first component 24 of the second implant part 20 is inserted into a fusion mold 52, so that it can be connected to the second component 27. The fusion mold 52 is in the form of a cylindrical mold which is provided with a lower part 53, a middle part 55 and a lid part 56. Formed on the lower part is a support element 54 which supports the first component 24 of the second implant part 20 upon insertion, whereas the middle part 55 grips around the first component. For connection of the components 24, 27, the volume 59, which is encompassed by the first component 24 at the first connection surface 25 thereof, is filled with the plastic of the second component 27 in powder form (not shown in FIG. 4) in order to form the second component 27 shown. For connection under application of heat, pressure and vacuum, the fusion mold 52 is closed with a stamp-like lid part 56, the mold side of which facing the first component is curved with a curved region 57 in the direction of the first component 24 situated in the fusion mold 52.

Figures 5A, 5B, 5C, 5D, 6, 7:
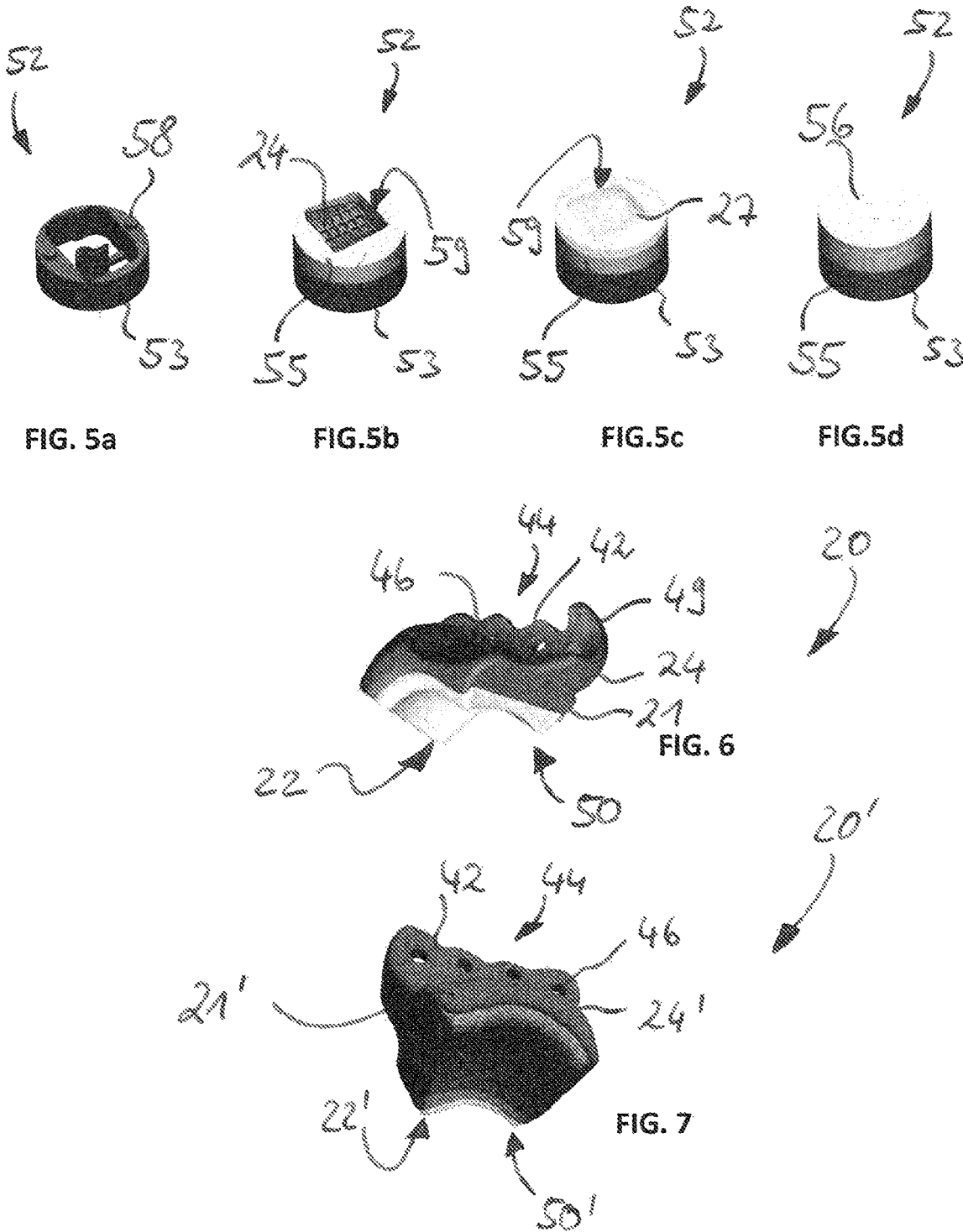
FIG. 5a-5d perspective side views of the third embodiment which show the connection of the first component to the second component of the second implant part in the fusion mold in the chronological sequence thereof.
FIG. 6 a perspective side view of a reverse side of a second implant part having connected components of a fourth embodiment.
FIG. 7 a perspective side view of a reverse side of a second implant part having connected components of a fifth embodiment.

FIGS. 5a to 5d show the chronological sequence of the fusion of the components as already outlined above, in that FIG. 5a depicts the lower part 53 of the substantially cylindrical fusion mold 52, the interior of which is provided with the support part 54 to support the first component 24 of the second implant part 20 that is to be inserted into said fusion mold 52. FIG. 5a further shows two holding projections 58 arranged relative to one another on the end-face edge facing the middle part 55, which is not depicted. In FIG. 5b, the mentioned middle part 55 grips around the first component inserted into the fusion mold 52, the curvature of which first component in the direction of the lower part 53 forms the volume 59. It is partially filled in FIG. 5c by the second component 27 in powder form, followed by application of heat, pressure and vacuum to the fusion mold in FIG. 5d, and so, after the fusion mold 52 has been closed by means of the lid 56 having the lid region 57 bulging in the direction of the lower part 53, the fused composite 50 can be formed at the second implant part 20.

FIG. 6 shows a perspective side view of a reverse side of a second implant part having connected components of a fourth embodiment, and FIG. 7 shows a perspective side view of a reverse side of a second implant part having connected components of a fifth embodiment.

It can be seen that, despite differently designed first and second connection surfaces 25, 25', 28, 28' on the two second implant parts 20, 20', they are outwardly identical, in particular provide an articular surface 22, 22' with functionality of identical effect.

Although the present invention has been described above on the basis of preferred exemplary embodiments, it is not restricted thereto, but is modifiable in a variety of ways. In particular, the invention can be altered or modified in many ways without departing from the essence of the invention.

The invention claimed is:

1. An implantable temporomandibular joint prosthesis comprising:
   a first implant part having an artificial condyle that is attachable to a lower jaw;
   a second implant part having an articular surface that is attachable to a cranium;
   wherein the articular surface forms an abutment for the artificial condyle;
   wherein the second implant part has a first component which is formed from a metallic material and which is attachable to the cranium and a second component which is formed from a plastic and which forms the articular surface;
   wherein the first component has a first connection surface and the second component has a second connection surface, and the first connection surface and the second connection surface are mutually engagingly and integrally connected to one another, and
   wherein the first component and the second component form an integrally bonded composite.

2. The temporomandibular joint prosthesis as claimed in claim 1, wherein the first connection surface is provided with recesses into which projections arranged on the second connection surface engage.

3. The temporomandibular joint prosthesis as claimed in claim 2, wherein the recesses in the first connection surface of the first component and the corresponding projections of the second component are homogeneous or inhomogeneous.

4. The temporomandibular joint prosthesis as claimed in claim 2, wherein the size of the recesses on the first connection surface of the first component is between 1 μm and 2000 μm.

5. The temporomandibular joint prosthesis as claimed in claim 1, wherein the first connection surface and the second connection surface are in the form of mutually congruent surfaces.

6. The temporomandibular joint prosthesis as claimed in claim 1, wherein the first connection surface is concave.

7. The temporomandibular joint prosthesis as claimed in claim 1, wherein the first component is made of titanium or a titanium alloy and the plastic of the second component is made of a thermoplastic.

8. The temporomandibular joint prosthesis as claimed in claim 1, wherein the first implant part is made of a ceramic, a PEEK (polyetherketone) material, a metallic material or a combination of these materials.

9. The temporomandibular joint prosthesis as claimed in claim 1, wherein the first component has an edge region which at least regionally grips around the second component.

10. The temporomandibular joint prosthesis as claimed in claim 1, wherein the first and the second implant part are detachably attachable to the lower jaw and the cranium, respectively, by a first and a second attachment part, respectively.

11. The temporomandibular joint prosthesis as claimed in claim 10, wherein the first attachment part has a first hole arrangement and the second attachment part has a second hole arrangement.

12. A method for producing an implantable temporomandibular joint prosthesis, at least comprising the following steps:
   providing a first implant part having an artificial condyle that is attachable to a lower jaw;
   providing a second implant part having an articular surface that is attachable to a cranium;
   wherein the articular surface forms an abutment for the artificial condyle;
   wherein the second implant part has a first component which is formed from a metallic material and which is attachable to the cranium and a second component which is formed from a plastic and which forms the articular surface;
   mutually engagingly and integrally connecting a first connection surface of the first component to a second connection surface of the second component, the first component and the second component fuse together to form an integrally bonded composite during the connecting.

13. The method as claimed in claim 12, wherein heat, and pressure or vacuum, are applied to the first component and the second component during connection of the first and second connection surfaces.

14. The method as claimed in claim 13, wherein the fused composite is formed at the first and the second connection surface by inserting the first component into a fusion mold and at least partially filling a volume encompassed by the first component in the region of the articular surface with the plastic of the second component in powder form before the application of heat, and pressure or vacuum.

15. The method as claimed in claim 14, wherein the fusion mold is multipieced and completely encloses the first component and the second component during connection thereof to one another to form a fused composite.

16. The temporomandibular joint prosthesis as claimed in claim 7, wherein the thermoplastic is PE-UHMW (ultra-high molecular weight polyethylene).

* * * * *